(12) United States Patent
Norton et al.

(10) Patent No.: US 8,195,291 B2
(45) Date of Patent: Jun. 5, 2012

(54) APPARATUS AND METHOD FOR OPTIMIZING CAPACITOR CHARGE IN A MEDICAL DEVICE

(75) Inventors: John D. Norton, New Brighton, MN (US); Anthony W. Rorvick, Champlin, MN (US)

(73) Assignee: Medtronic, Inc., Minneapolis, MN (US)

( * ) Notice: Subject to any disclaimer, the term of this patent is extended or adjusted under 35 U.S.C. 154(b) by 682 days.

(21) Appl. No.: 11/379,931

(22) Filed: Apr. 24, 2006

(65) Prior Publication Data

US 2006/0195148 A1 Aug. 31, 2006

Related U.S. Application Data

(63) Continuation-in-part of application No. 10/260,488, filed on Sep. 30, 2002, now abandoned.

(51) Int. Cl.
*A61N 1/39* (2006.01)
(52) U.S. Cl. .................................. 607/5; 607/7
(58) Field of Classification Search .................. 607/5, 7
See application file for complete search history.

(56) References Cited

U.S. PATENT DOCUMENTS

| | | | |
|---|---|---|---|
| 4,117,212 A | 9/1978 | Mead et al. | |
| 4,408,607 A | 10/1983 | Maurer | |
| 4,964,877 A | 10/1990 | Keister et al. | |
| 5,117,824 A | 6/1992 | Keimel et al. | |
| 5,131,388 A | 7/1992 | Pless et al. | |
| 5,163,427 A | 11/1992 | Keimel | |
| 5,439,482 A | 8/1995 | Adams et al. | |
| 5,470,341 A | 11/1995 | Kuehn et al. | |
| 5,554,174 A * | 9/1996 | Causey, III | 607/5 |
| 5,591,212 A | 1/1997 | Keimel | |
| 5,620,424 A | 4/1997 | Abramson | |
| 5,620,464 A | 4/1997 | Kroll et al. | |
| 5,766,797 A | 6/1998 | Crespi et al. | |
| 5,808,856 A | 9/1998 | Bischoff et al. | |
| 5,836,973 A | 11/1998 | Kroll | |
| 5,955,218 A | 9/1999 | Crespi et al. | |
| 6,032,075 A | 2/2000 | Pignato et al. | |
| 6,141,585 A | 10/2000 | Prutchi et al. | |
| 6,321,114 B1 | 11/2001 | Nutzman et al. | |
| 6,409,776 B1 | 6/2002 | Yan et al. | |
| 6,426,863 B1 | 7/2002 | Munshi | |
| 6,438,420 B1 | 8/2002 | Thompson | |
| 6,704,597 B1 | 3/2004 | Ware | |
| 7,076,296 B2 * | 7/2006 | Rissmann et al. | 607/9 |
| 2002/0052078 A1 | 5/2002 | Zheng et al. | |
| 2002/0071240 A1 | 6/2002 | Rorvick et al. | |
| 2002/0120302 A1 | 8/2002 | Lyden et al. | |

* cited by examiner

*Primary Examiner* — Michael Kahelin

(57) ABSTRACT

A medical device for electrical termination of an arrhythmic condition of a patient's heart in embodiments of the invention may include one or more of the following features: (a) at least one battery; (b) means for detection of an arrhythmic condition of a patient's heart; (c) at least one high voltage capacitor; (d) converter means for providing charging current from said battery to said capacitor; (e) means for maintenance of a charge on said capacitor between arrhythmia therapies; (f) controller means responsive to detection of an arrhythmic condition of said patient's heart and for providing a discharge control signal; and (g) discharge circuit means for delivering voltage stored on said capacitor to said patient's heart in response to said discharge control signal.

14 Claims, 6 Drawing Sheets

APPARATUS AND METHOD FOR OPTIMIZING CAPACITOR CHARGE IN A MEDICAL DEVICE

CROSS-REFERENCE TO RELATED APPLICATIONS

This application is a continuation-in-part of U.S. patent application publication No. U.S. 2004-0064154 A1 Ser. No. 10/260,488 entitled "APPARATUS AND METHOD FOR OPTIMIZING CAPACITOR CHARGE IN A MEDICAL DEVICE", filed Sep. 30, 2002, now abandoned.

FIELD OF THE INVENTION

The present invention relates generally to stimulators for medical treatment by means of voltage shocks, and more particularly to cardioverters and defibrillators and electrode systems for use in conjunction therewith.

BACKGROUND OF THE INVENTION

A defibrillator can be used to restore a normal heart rhythm by delivering an electrical shock to the heart when the heartbeat is dangerously fast due to ventricular tachycardia or ventricular fibrillation. Either of these conditions can reach a life-threatening point at which a person suddenly loses consciousness because the heart can no longer pump enough blood to meet the body's demand. For patients suffering from chronic arrhythmias involving ventricular tachycardia or ventricular fibrillation, a defibrillator can be surgically implanted in the patient's chest. The implanted defibrillator can be implanted into the chest of the patient during a minor surgical procedure.

An implantable cardioverter defibrillator (ICD) is a device that can be implanted in a patient's chest to monitor for and, if necessary, correct episodes of rapid heartbeat. If the heartbeat gets too fast (ventricular tachycardia), the ICD can stimulate the heart to restore a normal rhythm. In cases where the heartbeat is so rapid that the heart cannot effectively pump any blood (ventricular fibrillation), the ICD can provide an electric shock to "reset" the heartbeat.

The ICD gets its name from the two functions that it performs. First, the ICD sends small electrical charges to the heart to "reset" it during ventricular tachycardia. This process of converting one rhythm or electrical pattern to another is called cardioversion. Second, the ICD will send stronger charges to "reset" the heart if it begins ventricular fibrillation instead of beating. The act of stopping this potentially fatal quivering of the heart is called defibrillation. Although the main functions of the ICD are cardioversion and defibrillation, it can also be programmed to do anti-tachycardia and bradycardia pacing.

In anti-tachycardia pacing, when an ICD senses a fast but rhythmic heartbeat (tachycardia), it can release a series of low-intensity electrical pulses that gently interrupt the heart and allow it to return to a slower pace. In bradycardia pacing, when the ICD senses an abnormally slow heartbeat, it can send small electrical signals to pace the heart until it recovers and maintains a normal heart rate. These therapies are contrasted with both cardioversion and defibrillation, which involve high voltage shocks, which is the focus of the present invention.

In all of the ICD systems available today, a truncated capacitive-discharge shock is delivered by the ICD to electrodes that are positioned in, on, or near the heart. To generate the shock, existing ICD systems use an internal high current electrical battery cell connected to a step-up transformer and power conversion circuitry to charge one or more relatively small, but powerful, high voltage capacitors to provide a relatively high discharge voltage. When an electrical stimulation pulse is to be applied to the heart, the appropriate output switch is closed to connect the output capacitor to the cardiac tissue through the electrodes, thereby effectively "dumping" the charge stored in the output capacitor into the cardiac tissue. After the output decays to a predetermined output voltage, or after a predetermined shock duration has elapsed, the shock is truncated and the remaining energy in the output capacitor system is dissipated within the ICD system never being utilized or recovered.

The primary function of an ICD is to sense the occurrence of an arrhythmia, and to automatically apply an appropriate shock therapy to the heart aimed at terminating the arrhythmia. For example, if the ICD senses that the patient's heart is fibrillating then the ICD automatically delivers a high current shock to the patient's heart to defibrillate the organ. ICDs typically operate by first detecting the arrhythmia, then rapidly charging one or more storage capacitors contained within the device, and then quickly discharging the capacitor(s) to deliver the life saving shock therapy. However, a problem associated with rapidly charging a capacitor is that it creates a severe load on the battery. Thus reducing the battery's life.

An additional problem associated with the high voltage capacitors of an ICD is the amount of time it takes to charge the capacitors, typically about 5 to 20 seconds. Many studies have proposed that defibrillation and cardioversion shocks are most effective when delivered as quickly as possible following detection of arrhythmia. The chance of terminating an arrhythmia in a patient decreases as the length of time it takes for therapy to be delivered to the patient increases. Therefore, the shorter the charge time for the capacitors the more effective the defibrillation therapy. Typically, ICD battery sizes are proportional to the charging time. Therefore, the quicker the desired charging time, the larger the battery. In spite of this, it is desirable to make the ICD as small as possible and therefore large batteries are not desired and thus a balance must be struck between having a fast charging time and the size of the ICD.

Another problem involves providing a capacitor that maintains a high capacitance while at the same time has a reduced leakage current. The term "leakage current" refers to the measure of stray direct current flowing through a capacitor after DC voltage is impressed on it and is expressed in milliamps.

The dielectric of a capacitor has a very high resistance, which prevents the flow of DC current. However there are some areas in the dielectric, which allow a small amount of current to pass. The value of leakage current will continue to decrease while voltage is applied to the capacitor, until a very low steady state leakage current value is reached. However, as stated above, the present ICDs allow the remaining capacitor charge to dissipate after the arrhythmia has been treated. The longer capacitors are stored with no applied voltage, the higher the initial leakage current. Therefore, the constant recharging and the length between the recharging of the capacitors actually increases the amount of leakage current. A high leakage current can result in the poor performance and reliability of a capacitor. In particular, high leakage current results in a greater amount of charge leaking out of the capacitor once it has been charged. This is undesirable.

Another problem associated with the present ICDs, is that the remaining charge after the arrhythmia is treated is just dissipated within the ICD. While the charge dissipated is relatively minimal when compared to the shock charge, after hundreds of shocks the remaining charges can add up to a substantial shock. Typically, 16 remaining charges can add up to provide a defibrillation shock. Further, the dissipated remaining charges equate to energy taken from the battery and never put to use. Therefore, it would be desirable to capture these remaining charges and thus extend the life of the battery.

The discussion now turns to an ICD therapy, referred to as a high-power therapy, that delivers energy to a patient in approximately 10 milliseconds (ms). High-power therapy uses defibrillation capacitors at high energy defibrillation pulses (e.g. 0.1-35 joules (J)). The battery that powers the ICD does not directly provide energy to the patient's tissue. Instead, the ICD battery charges a high-energy, high-power capacitor system. High-energy, high-power capacitor system are also referred to as high-voltage therapy capacitor(s), main energy delivery capacitor(s), high-power capacitor(s), or other similar names. To date, all marketed ICDs use either aluminum or tantalum electrolytic capacitors for high-power therapy.

The amount of energy delivered by the capacitors is controlled by the voltage to which the capacitors are charged. The highest voltage to which the capacitors can be charged corresponds to the maximum energy therapy. The highest voltage typically relates to a few volts below the maximum rated voltage of the capacitors.

Electrolytic capacitors exhibit high leakage currents when operated near their maximum rated voltage. To minimize excessive power consumption, the high-voltage therapy capacitors are not maintained in a continuously charged state, but rather are charged only when an episode occurs. An episode is defined as the time period in which the ICD determines that a high-voltage therapy is required. Between episodes, the capacitors are allowed to rest uncharged. In the uncharged state, the charging efficiency of electrolytic capacitors degrades. Consequently, when the capacitors need to be charged at a later time, more energy and longer charge time is required. Therefore, ICDs are typically programmed to periodically charge the high-voltage capacitors in order to achieve charging efficiency. This process is referred to as reformation, as it is thought to "reform" the anodic oxide. Skilled artisans generally consider reformation as requiring that the capacitors be charged to their maximum rated voltage or the maximum energy voltage of the ICD. Charging the capacitors to their maximum rated voltage is referred to as the nominal reformation voltage of the device.

U.S. Patent No. 5,620,464 issued to Kroll et al. exemplifies a conventional process of periodically charging the capacitor without a continuous charge being applied to the high-voltage therapy delivery capacitor. In Kroll, the main energy delivery electrical circuit depicted in FIG. 6 for use in an ICD comprises a low power output primary defibrillator battery, a high power output intermediate power intensifying capacitor system, a switch for permitting the intermediate power intensifying capacitor system to rapidly charge a main energy delivery capacitor, and a main energy delivery capacitor. The main energy delivery capacitor is configured for discharging, in a first pulse, an electrical charge derived from the primary battery, and for discharging certain subsequent pulses of electrical charge derived from the intermediate power intensifying capacitor system. The circuit permits the ICD to deliver multiple closely spaced defibrillation pulses to a heart. The power intensifying system is periodically recharged from the primary power source. Kroll defines the power intensifying capacitor system as being separate and distinctly different in function from the main energy delivery capacitor. Kroll also specifies the types of energy storage devices which are suitable for the power intensifying system. Kroll is not suitable for use as a main energy delivery capacitor (i.e. therapy delivery capacitor).

For the foregoing reasons, there is a need for an ICD, which allows for a relatively long charging time and yet retains clinical efficacy to prolong battery life and provide for a smaller battery. There is also a need for an ICD providing a high voltage capacitor with very low leakage current so that the capacitor could be held at full charge thus reducing the adverse effects of rapid charging. There is also a need for an ICD that when an arrhythmia is detected the ICD can deliver therapy at the quickest possible moment without having to wait for a capacitor to charge thus increasing the efficacy of the delivered therapy.

BRIEF SUMMARY OF THE INVENTION

A medical device for electrical termination of an arrhythmic condition of a patient's heart in embodiments of the invention may include one or more of the following features: (a) at least one battery; (b) means for detection of an arrhythmic condition of a patient's heart; (c) at least one high voltage capacitor; (d) converter means for providing charging current from said at least one battery to said at least one capacitor; (e) means for maintenance of a charge on said at least one capacitor between arrhythmia therapies; (f) controller means responsive to detection of an arrhythmic condition of said patient's heart and for providing a discharge control signal; and (g) discharge circuit means for delivering voltage stored on said capacitor to said patient's heart in response to said discharge control signal.

A method for electrical termination of an arrhythmic condition of a patient's heart in embodiments of the invention may include one or more of the following features: (a) charging at least one high voltage capacitor with current from at least one battery, (b) detecting an arrhythmic condition of a patient's heart, (c) maintaining the charge on said at least one capacitor between arrhythmia therapies, (d) providing a controller means responsive to detection of an arrhythmic condition of said patient's heart, (e) generating a discharge control signal upon detection of an arrhythmic condition of said patient's heart; and (f) delivering a voltage stored on said capacitor to said patient's heart in response to said discharge control signal.

DETAILED DESCRIPTION OF THE PREFERRED EMBODIMENTS

Figure 1:
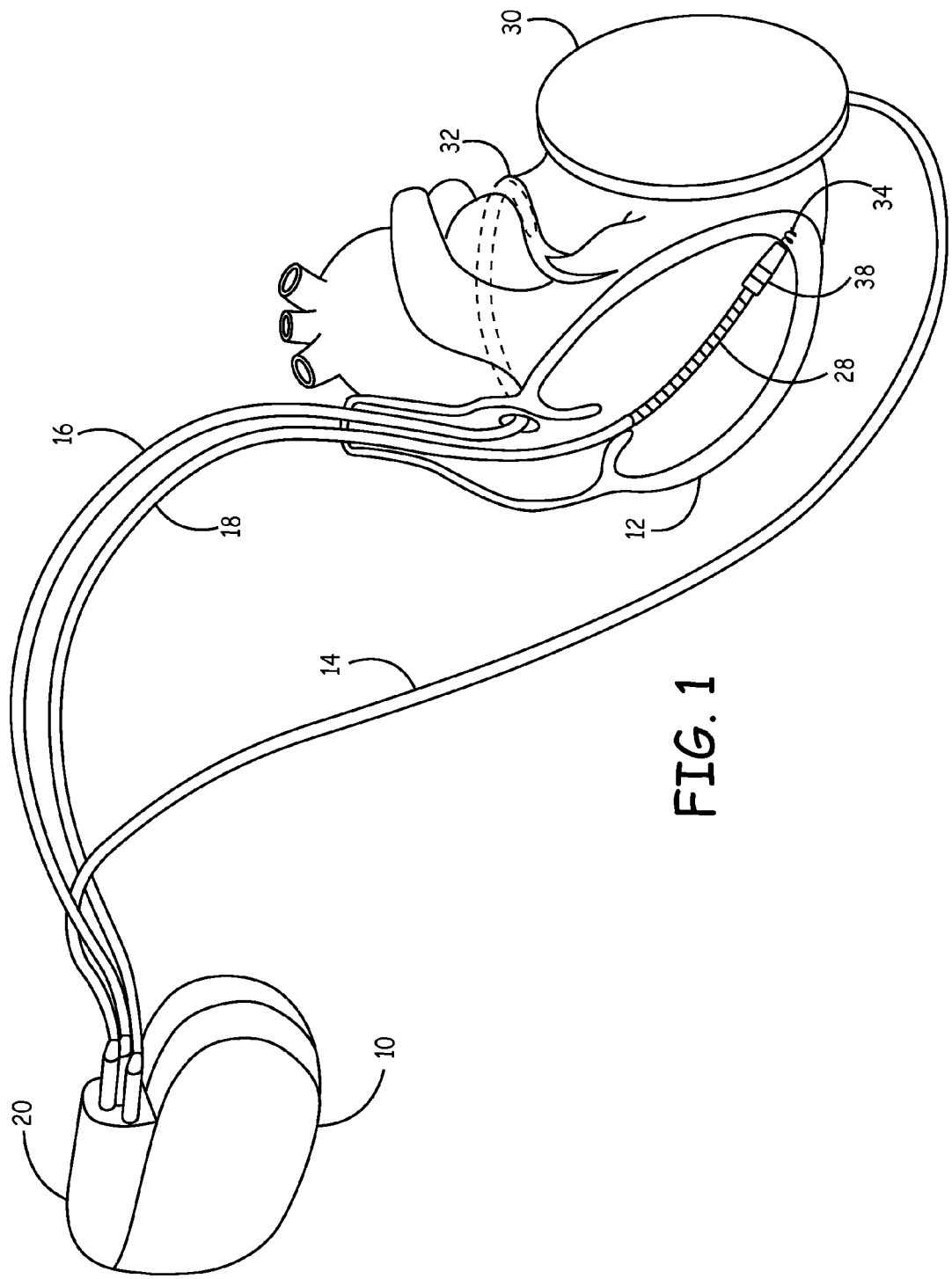
FIG. 1 is a drawing illustrating the general physical components of a pacemaker/cardioverter/defibrillator and lead system of the type in which the present invention may be advantageously practiced.

The following detailed description is to be read with reference to the figures, in which like elements in different figures have like reference numerals. The figures, which are not necessarily to scale, depict selected embodiments and are not intended to limit the scope of the invention. Skilled artisans will recognize that the examples provided herein have many useful alternatives that fall within the scope of the invention.

The present invention is not limited to implantable cardioverter defibrillators and may be employed in many various types of electronic and mechanical devices for treating patient medical conditions such as external cardioverter defibrillators, pacemakers, and neurostimulators. It is to be further understood; moreover, the present invention is not limited to medium current rate batteries and may be utilized for low and high current rate batteries. For purposes of illustration only, however, the present invention is below described in the context of medium current rate batteries and implantable cardioverter defibrillators.

The present invention is described generally in a system providing biphasic cardioversion pulses or shocks in a cardioversion system. However, it is fully contemplated that the present invention could be utilized in any type of pulse or shock delivery methodology utilizing any type of pulse of shock waveform without departing from the spirit of the invention. In the description of the preferred embodiment that follows, an implantable pacemaker/cardioverter/defibrillator in which the present invention is preferably implemented is capable of providing monophasic, biphasic, or any other cardioversion pulse or shock waveform. However, a variety of implantable leads and electrode systems may be employed, with more than one cardioversion electrode connected electrically in common to widen the cardioversion energy distribution across the heart. Such electrodes may include indwelling right ventricular, superior vena cava, and coronary sinus electrodes, active pulse generator case electrodes and/or epicardial and subcutaneous patch electrodes in various combinations of two or more. With a three electrode system, two of the electrodes are connected in common, and the energy distribution between the two common and the third electrode may lead to reduced energy sufficient to reliably cardiovert a heart in fibrillation or high rate malignant ventricular tachycardia.

To better understand the detailed description, certain terms are defined. Substantially continuously maintenance of a charging current refers to maintaining a capacitor in a fully or partially charged state. In one embodiment, the substantially continuous charge is terminated when a terminating condition occurs. For example, the charge current may be terminated after telemetry. Another terminating condition pertains to the time period prior to implant. In one embodiment, substantially continuously maintaining charge may be interpreted as more than 50% of the time.

Nominal positive charge is defined as the charge delivered by the battery to fully charge the capacitor(s) to deliver therapy to a patient.

An episode is defined as the time period in which the ICD determines that a high-voltage therapy is required.

FIG. 1 illustrates such a general implementation of an implantable pacemaker/cardioverter/defibrillator 10 and one possible selection of cardioversion electrodes on associated electrical leads 14, 16 and 18, and their relationship to a human heart 12. The leads 14, 16, and 18 are coupled to the pacemaker/cardioverter/defibrillator 10 by means of a multi-port connector block 20, which contains separate connector ports for each of the three leads illustrated. Each of the leads 14, 16, 18 comprise a large surface area cardioversion electrode, and lead 18 also comprises a pair of pace/sense electrodes (making it a tripolar lead) all as described below.

Unipolar lead 14 is coupled to a subcutaneous cardioversion electrode 30, which is intended to be mounted subcutaneously in the region of the left chest. Unipolar lead 16 is a coronary sinus (CS) lead employing an elongated coil, cardioversion electrode that is located in the coronary sinus of the heart. When positioned in the CS, the CS electrode extends around the heart from a point within the opening or ostium of the CS to a point in the vicinity of the left atrial appendage, as shown in broken line format at 32.

Tripolar lead 18 is provided with an elongated electrode coil 28 which is located in the right ventricle of the heart and functions as a third cardioversion electrode. Lead 18 also includes a first pace/sense electrode 34 and a second, closely spaced, pace/sense electrode 38. Electrode 34 takes the form of a distal helical coil, which is screwed into the myocardial tissue of the right ventricle. The second pace/sense electrode 38 is closely spaced to the electrode 34 for bipolar pacing and near field electrogram or R-wave sensing in the apex of the right ventricle. A more detailed description of the leads illustrated can be found in U.S. Pat. No. 5,163,427, herein incorporated by reference in its entirety.

Through testing at implantation of cardioversion efficacy across one of the three electrodes with the other two electrodes in common or with each of the other electrodes alone, a selection may be made of the most efficacious electrode selection. If only two electrodes are needed, then the third lead and electrode may be eliminated. Typically, it is expected that all three of the electrodes will be employed, with two connected electrically in common internally within the pulse generator 10 as described below.

Figure 2:
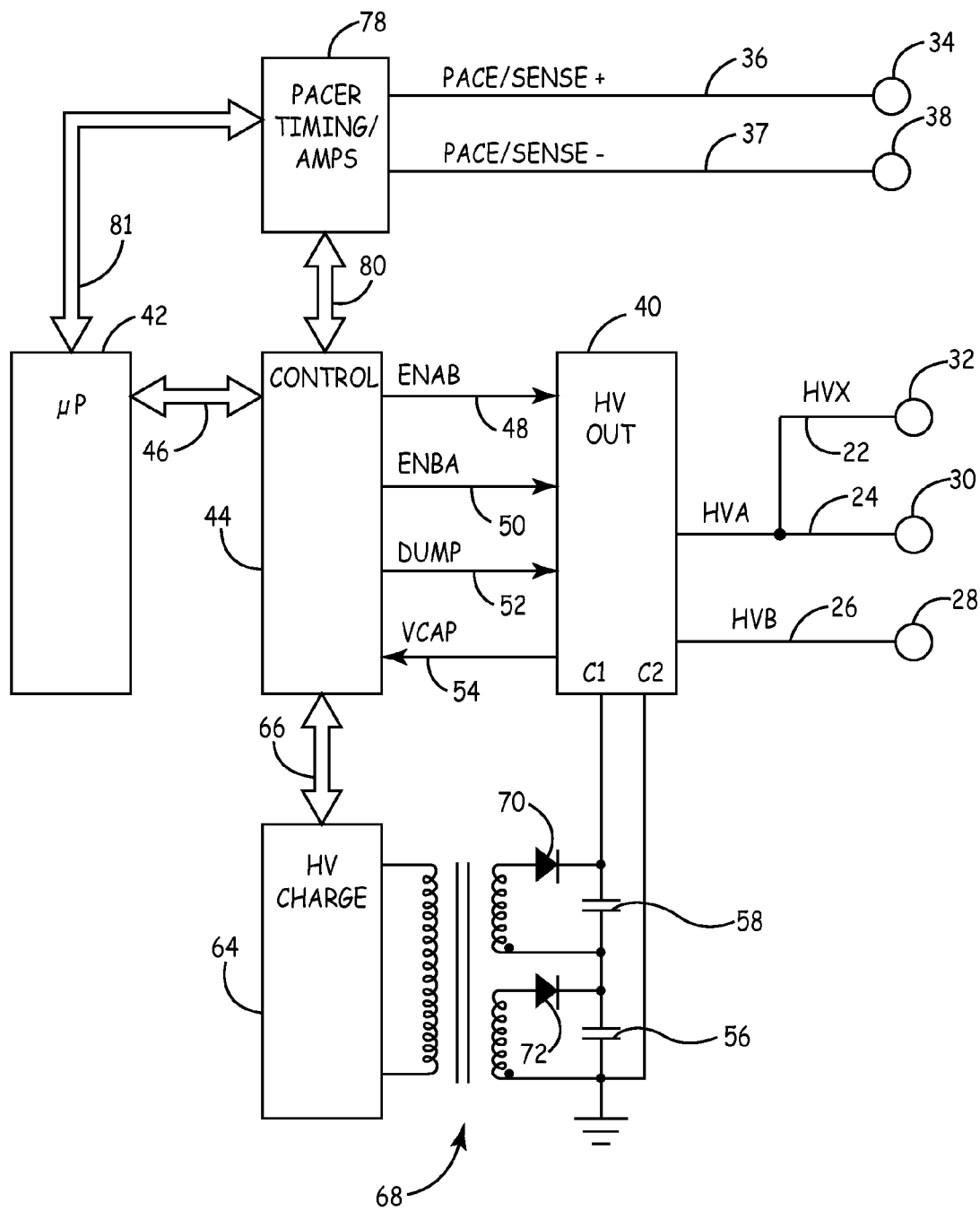
FIG. 2 is a functional block diagram illustrating the general interconnection of voltage conversion circuitry of the present invention with the primary functional components of an implantable pacemaker/cardioverter/defibrillator.

FIG. 2 is a block diagram illustrating the general interconnections of a voltage output circuit 40, a voltage charging circuit 64 and capacitor bank 56, 58 according to one embodiment of the present invention with a prior art implantable pacemaker/cardioverter/defibrillator. As illustrated, the device is controlled by means of a stored program in a microprocessor 42, which performs all necessary computational functions within the device. Microprocessor 42 is linked to control circuitry 44 by means of a bi-directional data/control bus 46, and thereby controls operation of the output circuitry 40 and the high voltage charging circuitry 64. On reprogramming of the device or on the occurrence of signals indicative of delivery of cardiac pacing pulses or of the occurrence of cardiac contractions, pace/sense circuitry 78 will awaken microprocessor 42 to perform any necessary mathematical calculations, to perform tachycardia and fibrillation detection procedures and to update the time intervals controlled by the timers in pace/sense circuitry 78.

The control circuitry 44 provides three signals of primary importance to the output circuitry 40 of the present invention. These include the first and second control signals discussed above, labeled here as ENAB, line 48, and ENBA, line 50, which govern the timing and duration of the two phases of the biphasic cardioversion pulse or shock. Also of importance is the DUMP signal on line 52, which initiates discharge of the output capacitors, and the VCAP signal on line 54, which is indicative of the voltage stored on the output capacitors C1, C2, and is applied to the control circuitry 44.

Figure 3:
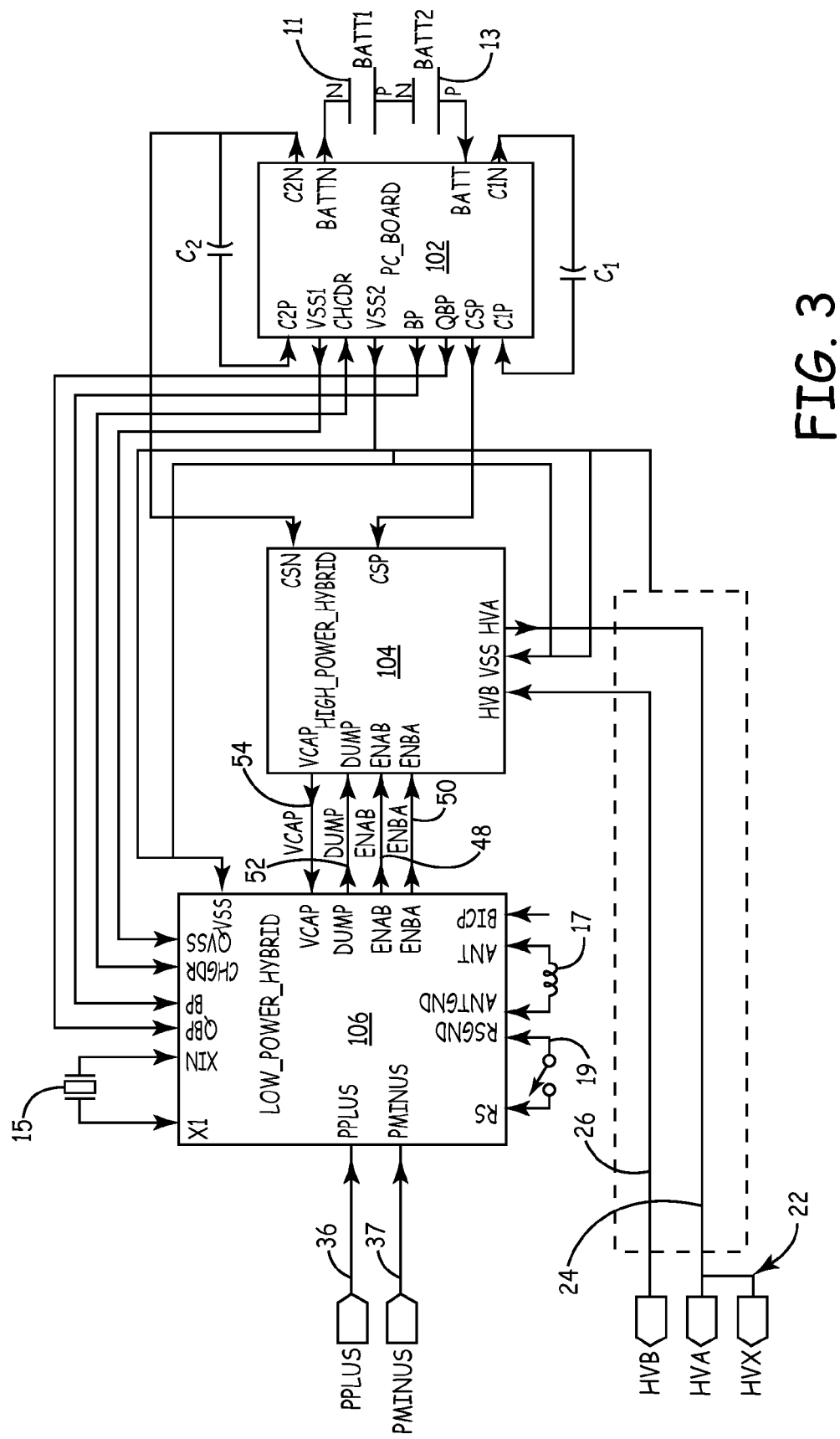
FIG. 3 is a schematic block diagram of the general components of a pacemaker/cardioverter/defibrillator employing a high voltage charging circuit.

As described above, a wide variety of cardioversion electrode bearing leads may be attached to two or all three cardioversion output terminals, labeled HVX, HVA, and HVB in FIG. 2, coupled to the connector block 20 bores. In the example illustrated in FIGS. 1 and 2, it will be assumed that the electrodes 28, 30 and 32 are coupled to the high voltage output circuitry 40 by means of connectors in the connector block 20 illustrated as conductors 22, 24 and 26, respectively. As shown in FIG. 3, conductors 22 and 24 labeled HVX and HVA are electrically connected in common so that an output shock may be delivered even if all three leads 18, 14 and 16 and electrodes 28, 30 and 32, respectively, are connected to the pulse generator as shown in FIG. 1 and described above.

The high voltage output circuit 40 includes a capacitor bank, including capacitors 56 and 58 (also referred to as a high-voltage therapy delivery capacitor(s)), which is discussed in more detail below, and diodes 70 and 72, used for delivering defibrillation pulses to the electrodes. In FIG. 2, the capacitor bank is illustrated in conjunction with the high voltage charging circuitry 64, controlled by the control/timing circuitry 44 by means of CHDR line 66. As illustrated, capacitors 56 (C1) and 58 (C2) are charged by means of a high frequency, high voltage transformer 68. Proper charging polarities are maintained by means of the diodes 70 and 72. VCAP line 54 provides a signal indicative of the voltage on the capacitor bank, and allows for control of the high voltage charging circuitry and for termination of the charging function when the stored voltage equals the programmed charging level.

The delivery of the biphasic cardioversion shock is controlled by the partial discharge of the voltage on the output capacitor bank in a first direction during a first phase logic signal on ENAB, line 48, and by further discharge of the remaining voltage in a second direction during closely timed second signal on ENBA, line 50. When ENAB is present, the first phase of the cardioversion pulse is delivered between the electrode(s) 30 and/or 32 and electrode 28. During a logic signal on ENBA, line 50, the second phase is delivered in the opposite direction between the same electrodes.

Pace/sense circuitry 78 includes an R-wave amplifier according to the prior art, or more advantageously as disclosed in U.S. Pat. No. 5,117,824 by Keimel et al, which is incorporated herein by reference in its entirety. However, the present invention is believed workable in the context of any known R-wave amplification system. Pace/sense circuitry 78 also includes a pulse generator for generating cardiac pacing pulses, which may also correspond to any known cardiac pacemaker output circuitry and includes timing circuitry for defining ventricular pacing intervals, refractory intervals and blanking intervals, under control of microprocessor 42 via control/data bus 80.

Control signals triggering generation of cardiac pacing pulses by pace/sense circuitry 78 and signals indicative of the occurrence of R-waves, from pace/sense circuitry 78 are communicated to control circuitry 44 by means of a bi-directional data bus 81. Pace/sense circuitry 78 is coupled to helical electrode 34 and ring electrode 38 of tripolar lead 18 through connector elements of the connector block 20 and associated adapters, if necessary, illustrated schematically as conductors 36 and 37.

The present invention constitutes an apparatus and method for maintaining a full or partial charge on a capacitor within an implantable medical device between therapies. The particular circuitry or components involved in the implementation of shock timing optimization are shown in specific detail. However, it is fully contemplated that alternate circuitry or components could be utilized, such as described in U.S. Pat. No. 6,438,420 (Thompson) herein incorporated by reference, without departing from the spirit of the invention. A number of additional expressions for input and output signals or terminals than those described above are used throughout, including:

CHGDR—Charge drive signal for driving the on/off switch in the primary winding of the flyback transformer at a duty cycle established by the relative on and off times.

VSS—VSS is the circuit ground, which may also appear labeled QVSS and may be connected to BATTN.

BATT—Battery positive power supply, which may also appear as B+ or as BP.

BATTN—Battery negative power supply.

PPLUS—Plus terminal for the pace/sense function.

PMINUS—Negative terminal for the pace/sense function.

ENBA—Enable signal commanding capacitor discharge from HVB to HVA (and HVX) and setting the duration of one phase of the biphasic pulse.

ENAB—Enable signal commanding capacitor discharge from HVA (and HVX) to HVB and setting the duration of the other phase of the biphasic pulse.

CSP—Charge store positive terminal.

C1P—Capacitor 1 positive terminal connection.

C1N—Capacitor 1 negative terminal connection.

C2P—Capacitor 2 positive terminal connection.

C2N—Capacitor 2 negative terminal connection.

CSN—Charge store negative terminal.

VDD—Internally generated programmable regulated power supply.

DUMP—DUMP signal initiates the internal self discharge of the capacitors C1, C2 to a load impedance.

OPTIN—Input terminal to the drive circuit optionally connected to an opto-coupler.

VIN—Input terminal to the drive circuit optionally connected to an input signal source.

VOUT—Output terminal of the drive circuit for supplying VDD voltage.

CSEN—Enable signal input terminal of the drive circuit optionally coupled to receive an opto-coupler command signal.

CSOUT—Output terminal of the drive circuit optionally coupled to drive an opto-coupler.

Other acronyms may appear in the description of the following drawings, which will be explained as necessary to understand the manner in which the present invention may be practiced in its preferred embodiment.

Turning now to FIG. 3, the circuit components of the pacemaker/cardioverter/defibrillator of the present invention are depicted and they include the batteries 11 and 13, the PC board 102, the high voltage output capacitors C1, C2 (56, 58 in FIG. 2), the high power hybrid board 104, the low power hybrid board 106, the crystal 15, the antenna 17, and the reed switch 19. The batteries 11 and 13 are coupled to the BATT and BATTN inputs of the PC board 102. Although two batteries are shown, it is fully contemplated that any type or combination of batteries could be utilized, such as a single cell battery, a dual cell battery, or a mixture of high current and low current cells, without departing from the spirit of the invention. The crystal 15 is coupled to the X1 and X1N inputs of the low power hybrid 106. The antenna 17 is coupled between the ANT and ANTGND inputs of low power hybrid 106 and the reed switch 19 is coupled between the RDSW and RSGND inputs of low power hybrid 106. The PPLUS and PMINUS terminals are coupled to respectively labeled pins of the low power hybrid 106, which contains the pace/sense circuitry 78 of FIG. 2.

The low power hybrid 106 includes the basic timing and control circuitry of the system, including the programming and telemetry functions, the electrogram sensing and pacing functions, the microprocessor and RAM/ROM memories, all implemented in both digital and analog circuits corresponding to blocks 42, 44 and 78 in FIG. 2. The low power hybrid 106 develops the CHGDR signal as well as the DUMP, ENBA and ENAB signals relevant to the operation of the high voltage output circuit of the present invention.

The PC board 102 corresponds to the high voltage-charging block 64 in FIG. 2, and also includes the step up transformer 110 and diodes 121,123. The relatively large output capacitors C1, C2 are electrically connected to the PC board 102 through the input terminals Cl N and Cl P and C2N and C2P, respectively. The PC board 102 presents the charge storage positive and negative signals CSP and CSN, respectively, to the high power hybrid 104. PC board 102 also includes an on-off control switch, responsive to the CHGDR signal from the low power hybrid 106, for supplying stepped up, rectified current to the output capacitors C1, C2, across which the voltage signals CSP, CSN are developed.

The high power hybrid 104 corresponds to the high voltage output block 40 illustrated in FIG. 2 and includes switching circuitry for delivery of voltage stored in capacitors C1 and C2 as monophasic, biphasic, or any other output pulse waveform. Delivery of the output pulses is controlled by the low power hybrid 106 via ENAB and ENBA lines 48 and 50, respectively. Similarly, the HVA line 24, which is coupled in common to the HVX line 22, and the HVB line 26 are coupled to the HVA and HVB output pins of high power hybrid 104. The high voltage discharges forming the cardioversion shocks are generated from the high power hybrid 104 and conducted to the HVA and HVB output terminals and the cardioversion electrode system employed as described above.

With reference to FIGS. 2 and 3 again, one embodiment of the present invention is described. In one embodiment, capacitors 56 and 58 are high voltage capacitors with an extremely low leakage current. An exemplary low leakage capacitor is described in U.S. Pat. No. 5,808,856 (Bischoff, et. al.), U.S. Pat. No. 6,426,863 (Munshi) and U.S. Pub. No. 2002/0052078 (Zheng et. al.). While it is preferable that a low leakage capacitor be utilized for the present embodiment, it is contemplated that any high voltage capacitor could be utilized without departing from the spirit of the invention. Further, it is fully contemplated that the present invention could utilize one or more individual capacitors as well as multiple capacitors utilizing a wide range of capacitor voltages. Nevertheless, preferably capacitors 56 and 58 are high voltage low leakage capacitors having a combined energy loss to leakage on the order of tens of μW. Low leakage rate capacitors 56 and 58 are chosen so that they can be fully or partially charged and then retain a substantial part of that charge over a relatively extended period of time.

In this embodiment batteries 11 and 13 are used to charge capacitors 56 and 58 as discussed above. Preferably batteries 11 and 13 are medium rate batteries or a two cell combination of a low rate and high rate battery. However, as stated above, it is fully contemplated that any combination or any type of battery including a single battery could be used without departing from the spirit of the invention. The medium rate battery is smaller in size compared to a high rate battery and thus volume within the implantable device can be significantly reduced. Nevertheless, it is fully contemplated that a high rate battery could be utilized within the implantable device to charge capacitors 56 and 58. However, with a medium rate battery, capacitors 56 and 58 can be charged over a relatively long time, such as between 20 seconds to several minutes. As stated above this is better for batteries 11 and 13 and will increase their lifetime, which thus increases the implantable device's lifetime. Further, since it is also desirable to minimize the volume occupied by the implantable devices as well as their mass to further limit patient discomfort, a smaller medium rate battery is preferred.

Figure 4:
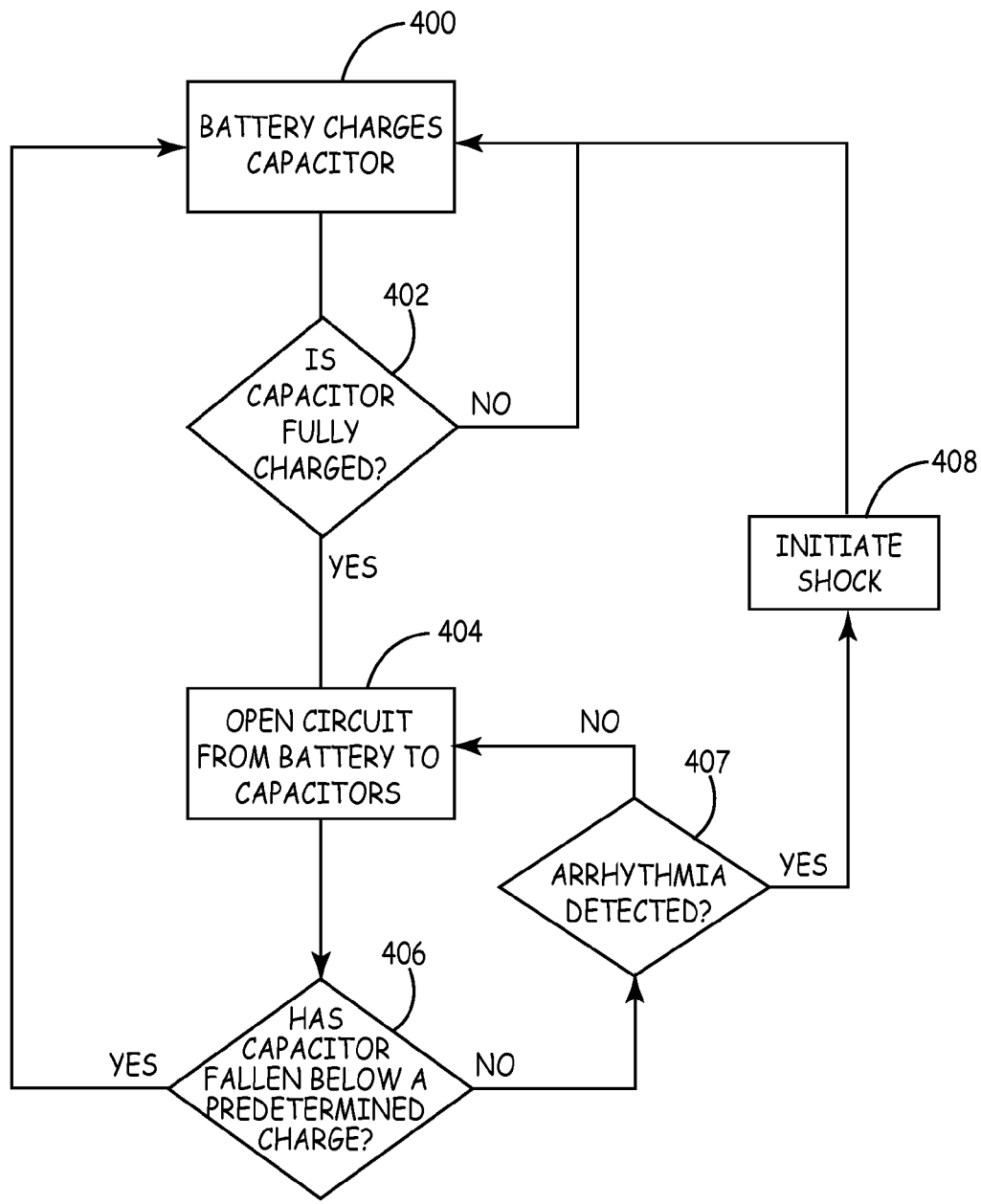
FIG. 4 is a flow diagram of an embodiment for capacitor optimization of the present invention.
Figure 5:
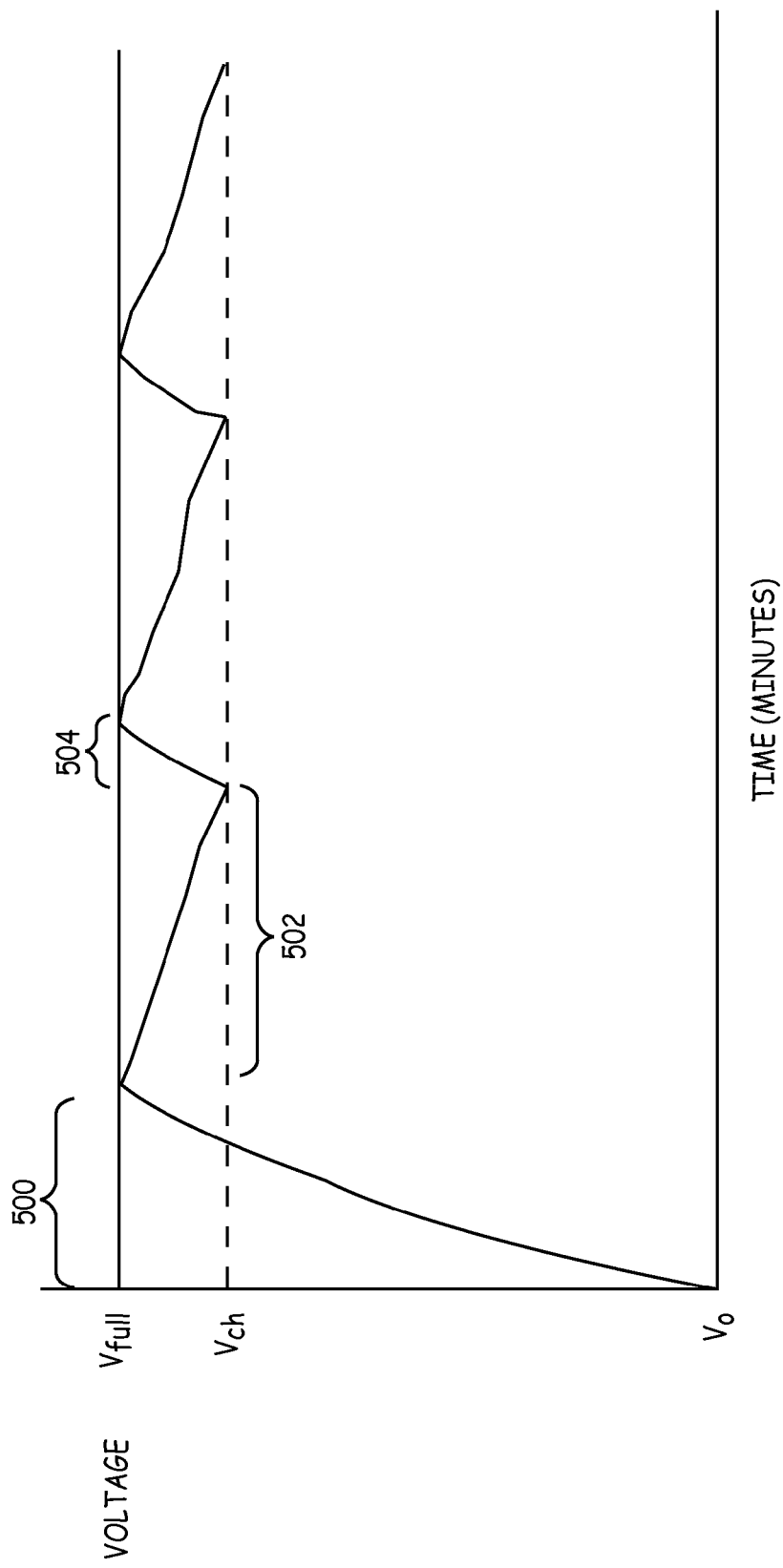
FIG. 5 is a table representing a capacitor optimization embodiment of the present invention.

With reference to FIGS. 4 and 5, a flow diagram of an embodiment for capacitor optimization and a table of an embodiment for capacitor optimization is shown. In the present embodiment, batteries 11 and 13 first charge capacitors 56 and 58 to an initial level, which is shown as state 400. Preferably capacitors 56 and 58 are fully charged as represented by region 500 of FIG. 5, however, it is contemplated that capacitors 56 and 58 could be partially charged, which would require a shorter charging time upon detection of an arrhythmia, and thus a shorter time until a therapeutic shock could be delivered. Microprocessor 42 continuously receives the VCAP signal giving the voltage levels of capacitors 56 and 58 from control circuitry 40 via data bus 46. Processor 42 monitors the voltage level of capacitors 56 and 58 and determines if the capacitor is fully charged, as is shown in state 402. If capacitors 56 and 58 are not fully charged, processor 42 maintains charging of capacitors 56 and 58, thus returning to state 400. However, if capacitors 56 and 58 are fully charged, then processor 42 creates an open circuit between batteries 11 and 13 and capacitors 56 and 58, as shown in state 404. It is contemplated that processor 42 could create this open circuit by opening a relay switch, turning on or off a transistor, or utilizing any other switching methods known in the art.

Processor 42 then determines from the VCAP signal whether capacitors 56 and 58 have fallen below a predetermined charge, as shown in state 406. Preferably this predetermined level is chosen during implantation of the implantable medical device and is chosen to be a level, which can provide an adequate shock to correct an arrhythmia. Over a period of hundreds of minutes, low leakage capacitors 56 and 58 will eventually loose enough charge through current leakage that their charge will fall to a predetermined level represented by region 502 in FIG. 5. When the charge level in capacitors 56 and 58 falls below this predetermined level, microprocessor 42 instructs control circuitry 40 to begin charging capacitors 56 and 58 as represented by region 504. Thus processor 42 returns to state 400. If capacitors 56 and 58 have not fallen below the predetermined level, processor 42 determines whether an arrhythmia has been detected, shown as state 407 in FIG. 4. If no arrhythmia is detected then processor 42 returns to state 404 to assure that batteries 11 and 13 are isolated from capacitors 56 and 58. If an arrhythmia is detected, processor 42 delivers a therapeutic shock at the quickest possible moment, as shown in state 408. It is well known that the shock cannot be delivered during certain times, therefore, the shock is delivered at the quickest possible moment. As stated above, this quickly delivered therapy substantially increases the efficacy of the therapy.

After the therapeutic shock is delivered, processor 42 returns to state 400 where batteries 11 and 13 are reconnected with capacitors 56 and 58 and begin charging them. Thus the remaining charge left after the therapy is not lost, since capacitors 56 and 58 quickly begin recharging after the therapy. Once capacitors 56 and 58 are fully charged again (state 402), processor 42 then instructs control 40 to stop charging capacitors 56 and 58 (state 404). This process then repeats continuously until an arrhythmia is detected (state 407) in which case, as described above, capacitors 56 and 58 are discharged to provide a properly timed shock to the heart (state 408).

After a shock event, the present embodiment is preferably implemented so that the total time to second shock is approximately 30 seconds. As is known, sometimes the first shock event is unsuccessful in stopping an arrhythmia; therefore, a second shock event is sometimes needed. The present invention is still able to supply a second shock in plenty of time even though a medium rate battery is being implemented. In the alternative, a high voltage binary battery could be implemented where if a second shock event was necessary, the binary battery would provide a high voltage charge to capacitors 56 and 58 within 5 to 20 seconds.

Figure 6:
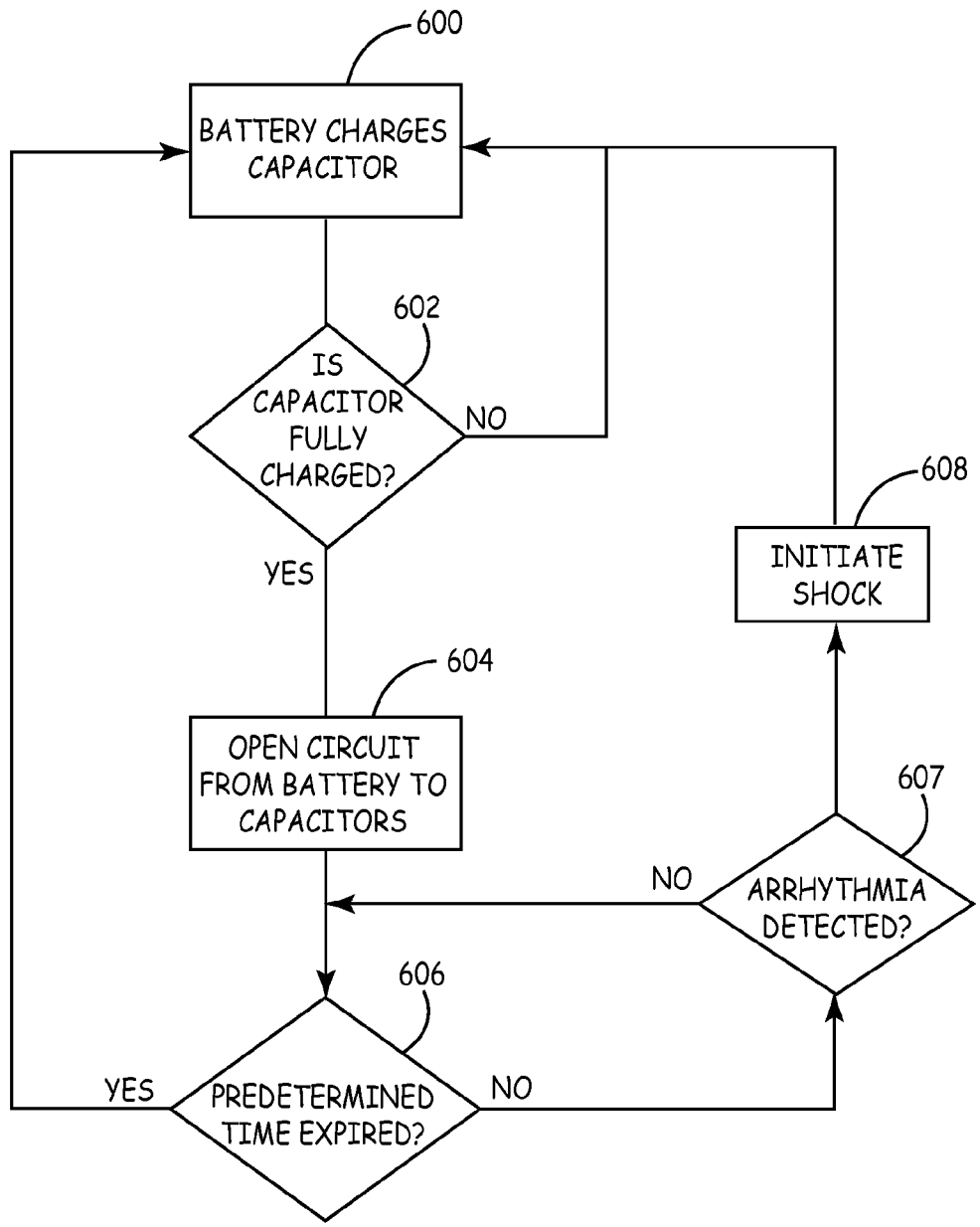
FIG. 6 is a flow diagram of an embodiment for capacitor optimization of the present invention.

With reference to FIG. 6, a flow diagram of an embodiment for capacitor optimization is shown. In this embodiment, batteries 11 and 13 first charge capacitors 56 and 58 to an initial level, which is shown as state 600. Processor 42 monitors the voltage level of capacitors 56 and 58 and determines if the capacitor is fully charged, as is shown in state 602. If capacitors 56 and 58 are not fully charged, processor 42 maintains the charging of capacitors 56 and 58, thus returning to state 600. However, if capacitors 56 and 58 are fully charged, then processor 42 creates an open circuit between batteries 11 and 13 and capacitors 56 and 58, as shown in state 604. It is contemplated that processor 42 could create this open circuit by opening a relay switch, turning off or on a transistor, or utilizing any other switching methods known in the art.

Processor 42 then determines whether a predetermined amount of time has expired since capacitors 56 and 58 were fully charged as represented by state 606. Preferably this predetermined time period represents the time it takes before the leakage current of capacitors 56 and 58 have drained the charge on capacitors 56 and 58 to a level just above one which could provide a shock to correct an arrhythmia event. Over a period of hundreds of minutes, low leakage capacitors 56 and 58 will eventually loose enough charge through current leakage that their charge will fall below an effective charge. When this predetermined time period has passed, microprocessor 42 instructs control circuitry 40 to begin charging capacitors 56 and 58 as represented by region 604. Thus processor 42 returns to state 600. If the predetermined time period has not passed, processor 42 determines whether an arrhythmia has been detected, shown as state 607. If no arrhythmia is detected then processor 42 returns to state 606 to determine whether the predetermined time limit has passed. If an arrhythmia is detected, processor 42 delivers a therapeutic shock at the quickest possible moment, as shown in state 608. After the therapeutic shock is delivered, processor 42 returns to state 600 where batteries 11 and 13 are reconnected with capacitors 56 and 58 and begin charging them.

In another embodiment, batteries 11 and 13 supply a continual medium rate charge to capacitors 56 and 58 to maintain them at a full or partial charge. In this embodiment, once capacitors 56 and 58 are preferably at maximum charge batteries 11 and 13 only have to supply capacitors 11 and 13 with enough charge to replace the charge lost due to the leakage current in order to keep capacitors 56 and 58 at a substantially full charge. Since the leakage current is so low for capacitors 56 and 58, the amount of charge required from batteries 11 and 13 is low. Thus, the continual charging does not deplete batteries 11 and 13. In comparison the leakage current of capacitors 56 and 58 is lower than the current required by processor 42. In this embodiment, capacitors 56 and 58 preferably don't fall below a full charge. Similar to above, when an arrhythmia is detected, a shock can be delivered at the quickest possible moment thus increasing the efficacy of the shock and the more likely normal cardiac rhythm is successfully restored.

In another embodiment batteries 11 and 13 charge a low leakage capacitor, which in turn charges a high voltage capacitor. In this embodiment, capacitors 56 and 58 could be any type of capacitors and would not have to be low leakage capacitors. Batteries 11 and 13 would continuously charge the low leakage capacitor and in the event of an arrhythmia, the low leakage capacitor would discharge through transformer 68, thus almost instantly charging capacitors 56 and 58, which would discharge immediately upon reaching full charge. It is noted that the low leakage capacitor retains any charge not delivered to capacitors 56 and 58 so that no charge is wasted. It is also contemplated that any combination of the embodiments listed above could be utilized without departing from the spirit of the invention.

In another embodiment a binary, chemical or thermal battery is utilized to power a "lifeboat" type of defibrillator. This device would be essentially inactive except for a monitoring circuit, such as in a pacemaker until an arrhythmia was detected. Upon detection, the binary (or thermal, chemical) battery would be activated and provide a high voltage shock at the quickest possible moment.

In another embodiment, a control module is used to intelligently optimize charging current for one or more high-voltage therapy delivery capacitors. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality. In this embodiment, the control module tracks a number of relevant variables. For example, control module tracks the amount of time it takes to fully charge the high-voltage therapy delivery capacitors relative to a particular level of charging current for substantially continuous charging the high-voltage therapy delivery capacitors. In another embodiment, the control module optimizes the level of the substantially continuous charging current versus the need to minimize the loss of power. In one embodiment, the optimization occurs by control module accessing, from memory, data from historical episodes. To illustrate, after a first episode, the control module may determine that the charging current could be maintained at a lower level to achieve optimal results. Therefore, before the second episode occurs the control module intelligently decreases the charging current by a certain level. In one embodiment, the charging current is incrementally decreased a standard level (e.g. a percentage such as 10 percent of the previous substantially continuous charging current.) In another embodiment, the control module intelligently determines the optimal level of the substantially continuous charging current based upon the historical data.

It will be appreciated that the present invention can take many forms and embodiments. The true essence and spirit of this invention are defined in the appended claims, and it is not intended that the embodiment of the invention presented herein should limit the scope thereof.

What is claimed is:

1. A system for the treatment of an arrhythmia of a patient comprising:
 a battery;
 a first capacitor;
 an arrhythmia detector capable of being coupled to the patient, the detector operable to detect an arrhythmia of the patient;
 an output circuit coupled to the first capacitor, to the patient and to the arrhythmia detector, the output circuit operable to deliver a shock voltage from the first capacitor to the patient responsive to the arrhythmia detector having detected an arrhythmia of the patient; and
 a charging module coupled to the battery, the first capacitor and the arrhythmia detector, the charging module adapted to:
  charge the first capacitor from the battery, responsive to the output circuit having delivered the shock voltage to the patient and without determining the patient's state, terminate the charging the first capacitor responsive to the first capacitor having the shock voltage, maintain the shock voltage on the first capacitor responsive to the terminating the charging the first capacitor, and terminate the maintaining the shock voltage on the first capacitor responsive to the detection of an arrhythmia.

2. The medical device of claim 1, further comprising:
a low leakage capacitor operably coupled to the battery and to the charging module,
the low leakage capacitor charged by the battery, and, responsive to the detected arrhythmia of the patient, the charging module charges the first capacitor from the low leakage capacitor and when the first capacitor is charged to a level suitable for the therapeutic shock, the output circuit delivers the shock.

3. The medical device of claim 1, wherein the first capacitor is discharged to provide a shock to the patient's heart upon the detection of an arrhythmia.

4. The medical device of claim 1, further comprising:
a voltage detector coupled to the charging module; and
a switch coupled to the first capacitor and the charging module, wherein the voltage detector detecting a predetermined voltage level on the first capacitor and the switch creating an open circuit between the first capacitor and the charging module.

5. The medical device of claim 1, wherein the charging module comprises a switch for creating an open circuit between the first capacitor and the charging module for a predetermined amount of time.

6. The medical device of claim 1, wherein the charging module charges the first capacitor to a voltage level appropriate for delivery of a therapeutic shock to the patient.

7. The medical device of claim 1, wherein the charging module charges the first capacitor to a voltage level that is less than the level appropriate for delivery of a therapeutic shock to the patient but at a level that is not fully discharged.

8. The medical device of claim 4, wherein, when the voltage level falls to a pre-determined threshold, the switch couples the charging module and the first capacitor, and the charging module charges the first capacitor.

9. A method for treating an arrhythmia of a patient comprising the steps of:
charging a first capacitor;
terminating the charging responsive to the first capacitor having a shock voltage;
maintaining the shock voltage on the first capacitor responsive to the terminating the charging;
detecting an arrhythmia of the patient;
terminating the maintaining the shock voltage on the first capacitor responsive to the detecting an arrhythmia;
delivering the shock voltage from the first capacitor to the patient responsive to the detecting an arrhythmia;
recharging the first capacitor responsive to the delivering the shock voltage without determining the patient's state; and
terminating the recharging responsive to the first capacitor having the shock voltage.

10. The method of claim 9 further comprising creating an open circuit between the first capacitor and the charging module after a predetermined voltage level is reached on the first capacitor.

11. The method of claim 9 further comprising creating an open circuit for a predetermined amount of time between the first capacitor and the charging module after a predetermined voltage level is reached on the first capacitor.

12. The method of claim 9, further comprising maintaining the voltage on the first capacitor at a voltage level appropriate for delivery of a therapeutic shock to the patient's heart.

13. The method of claim 9, further comprising maintaining the voltage on the first capacitor at a charge level that is less than the level appropriate for delivery of a therapeutic shock to the patient's heart but at a level that is not fully discharged, between arrhythmia episodes.

14. The method of claim 10, further comprising:
charging the first capacitor when the voltage level falls to a pre-determined threshold.

* * * * *